US008690953B2

(12) United States Patent
Ribic

(10) Patent No.: US 8,690,953 B2
(45) Date of Patent: Apr. 8, 2014

(54) PROSTHETIC IMPLANT SYSTEM INCORPORATING CONTRAST AGENT

(75) Inventor: Sonja Ribic, Winterthur (CH)

(73) Assignee: Zimmer, GmbH, Winterthur (CH)

(*) Notice: Subject to any disclaimer, the term of this patent is extended or adjusted under 35 U.S.C. 154(b) by 1247 days.

(21) Appl. No.: 11/464,270

(22) Filed: Aug. 14, 2006

(65) Prior Publication Data

US 2008/0188937 A1   Aug. 7, 2008

(30) Foreign Application Priority Data

Aug. 16, 2005   (EP) ..................................... 05017771

(51) Int. Cl.
*A61F 2/28* (2006.01)

(52) U.S. Cl.
USPC .................. 623/20.16; 623/23.48; 623/23.62; 606/912

(58) Field of Classification Search
USPC ............ 623/20.16, 22.39, 23.19, 23.2, 23.23, 623/23.25, 23.28, 23.37, 23.46, 23.48, 623/23.58, 23.62
See application file for complete search history.

(56) References Cited

U.S. PATENT DOCUMENTS

| | | | |
|---|---|---|---|
| 5,938,698 A | 8/1999 | Sandoz et al. | |
| 6,200,338 B1* | 3/2001 | Solomon et al. | 623/1.34 |
| 6,599,448 B1* | 7/2003 | Ehrhard et al. | 252/582 |
| 2002/0118595 A1 | 8/2002 | Miller | |
| 2002/0156483 A1 | 10/2002 | Voellmicke et al. | |
| 2002/0177866 A1* | 11/2002 | Weikel et al. | 606/192 |
| 2003/0093153 A1* | 5/2003 | Banick et al. | 623/17.11 |
| 2006/0282168 A1* | 12/2006 | Sherman et al. | 623/18.12 |
| 2007/0055382 A1* | 3/2007 | Osorio et al. | 623/23.62 |
| 2007/0191708 A1* | 8/2007 | Gerold et al. | 600/431 |
| 2007/0270691 A1* | 11/2007 | Bailey et al. | 600/431 |

FOREIGN PATENT DOCUMENTS

| | | |
|---|---|---|
| DE | 19926816 | 2/2001 |
| EP | 0834294 | 4/1998 |
| WO | WO 9918894 A1 * | 4/1999 |

OTHER PUBLICATIONS

Biomaterial in Orthopedics; Michael J. Yaszemski, Kai-Uwe Lewandrowski, Debra J. Trantolo, Donald L. Wise, Vasif Hasirci, and David E. Altobelli; Published by Informa Health Care 2003; ISBN 082474294X, 9780824742942; pp. 267-269.*

"European Application Serial No. 05017771.6, European Search Report mailed Mar. 15, 2006", 3 pgs.

* cited by examiner

*Primary Examiner* — Bruce E Snow
*Assistant Examiner* — Melissa Hoban
(74) *Attorney, Agent, or Firm* — Schwegman Lundberg & Woessner, P.A.

(57) ABSTRACT

The invention relates to an operation system comprising at least one implant and means for the fastening of the implant to a bone, wherein the fastening means include at least one solid spacer, which can be formed of hardened bone cement and is arranged between the implant and the bone in the implanted state, and hardenable liquid bone cement which can be introduced into hollow spaces or intermediate spaces present between the spacer and the implant and/or between the spacer and the bone and wherein the spacer, on the one hand, and the liquid bone cement, on the other hand, are provided with contrast agents chosen in dependence on an imaging observation process or inspection process, in particular an X-ray process, to be used in or after the operation such that the spacer and the liquid cement can be distinguished from the surroundings and from one another on the observation or inspection of their position, in particular in an X-ray.

24 Claims, 2 Drawing Sheets

PROSTHETIC IMPLANT SYSTEM INCORPORATING CONTRAST AGENT

Figure 1:
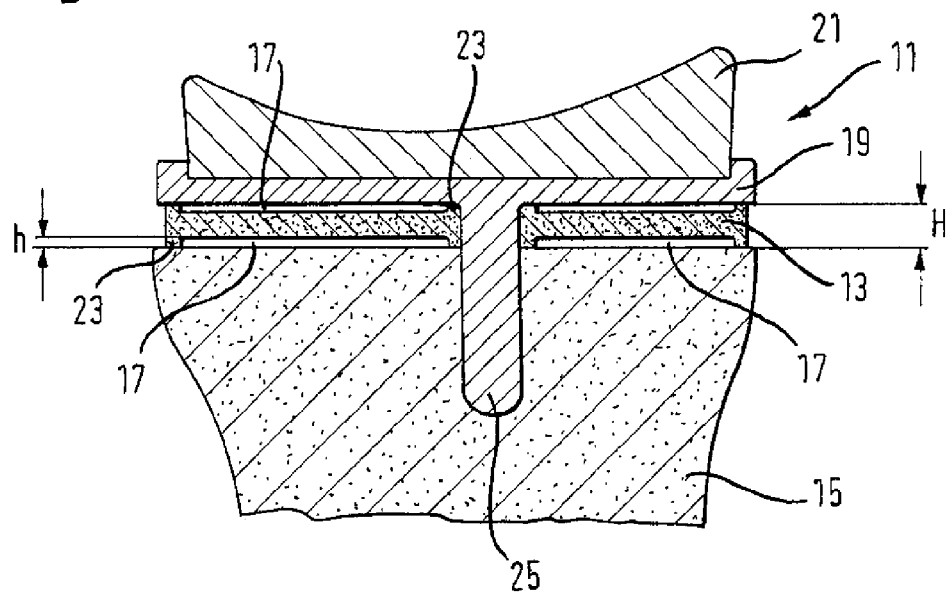

This application claims priority to European Patent Application Number EP05017771, filed on Aug. 16, 2005.

The invention relates to an operation system comprising at least one implant and means for the fastening of the implant to a bone, with the fastening means including, in one embodiment thereof, at least one solid spacer, which can be formed of hardened bone cement and is arranged between the implant and the bone in the implanted state, and, in certain embodiments, hardenable liquid bone cement which can be introduced into hollow spaces or intermediate spaces present between the spacer and the implant and/or between the spacer and the bone.

Operation systems of this type are used, for example, in knee surgery where artificial knee joints are inserted. Correspondingly made implants are fastened to the tibial bone and to the femoral bone for this purpose. The implants are in particular so-called tibial platforms which serve as carriers for support shells and femoral condyle parts matched to the support shells. In many cases, the bones are provided with planar resection surfaces for the preparation of the implant fastening.

Spacing between the implants and these resection surfaces can be set with the aid of so-called "spacers" which are placed between the bone and the implant. The fastening of these spacers to the implant and to the bone takes place by the introduction of liquid bone cement into hollow spaces or intermediate spaces which, on a corresponding design of the spacers, are present between it and the implant or the resection surface at the bone.

Liquid bone cement has typical hardening times of much less than 30 minutes and, in the hardened state, also provides a shape-matched connection in the micro-structural region between the spacer and the implant or between the spacer and the bone. Important properties of bone cement include biocompatibility, good processing capability and the capability of being flowable for a sufficiently long time during the introduction phase, on the one hand, and of hardening as fast as possible after the introduction, on the other hand.

Spacers made of bone cement are described in EP 834 294 A1. In contrast to metallic spacers which are anchored to the implant without bone cement, spacers anchored to the implant with bone cement generate less wear on use even when they consist of bone cement themselves. Beneficially, the hollow spaces and intermediate spaces to the spacer can be completely filled with liquid bone cement so that a connection with good tensile strength is established to the spacer by the preparation with liquid bone cement.

To be able to recognize the once liquid bone cement in the X-ray, a suitable contrast agent can be added to the bone cement and thus to "dye" it so-to-say. The concentration or proportion of contrast agent can be selected such that the once liquid bone cement can be easily distinguished from a metallic implant or spacer in the X-ray.

The dyeing of the liquid bone cement, however, still does not solve the problem that the surgeon cannot recognize in the X-ray whether the liquid bone cement completely fills up the existing hollow spaces or intermediate spaces to the spacer.

The intermediate inspections and periodic follow-up inspections subsequent to the operation are usually carried out with imaging processes, in particular with X-ray processes. It is, however, practically impossible to determine the contact between the liquid cement and the spacer since a spacer made of bone cement cannot be distinguished from air or from its environment.

It is therefore the object of the invention to further develop an operation system of the initially named kind such that the surgeon can check in a simple and reliable manner whether the hollow spaces or intermediate spaces are filled with bone cement in the desired manner.

In accordance with the invention, the spacer, on the one hand, and the liquid bone cement, on the other hand, are provided with contrast agents chosen in dependence on an imaging observation process or inspection process, in particular an X-ray process, to be used in or after the operation such that the spacer and the liquid cement can be distinguished from the surroundings and from one another on the observation or inspection of their position, in particular in an X-ray.

The invention is based on the idea of providing the liquid bone cement and the spacer respectively with a contrast agent, with this taking place, however, in a manner matched to one another in order to make the spacer distinguishable from the liquid bone cement.

Trials with imaging processes have shown that it is possible to add contrast agent in a manner required for the distinction, i.e. to obtain sufficient contrast between the bone, spacer, bone cement and implant by the "dyeing" of the spacer with contrast agent without impairment of the mechanical properties of the bone cement.

It is achieved by this simple and simultaneously extremely effective measure that the spacer, on the one hand, and the liquid bone cement, on the other hand, differ so much from one another, in particular in an Xray, that the respective components can be recognized separately from one another by their different "dyeing" or "shading".

It was unexpectedly found that, in accordance with an embodiment of the invention, the spacer and the liquid bone cement can be provided with different concentrations or proportions of in particular the same contrast agent such that a sufficient contrast is present between the spacer and the liquid bone cement in the X-ray and the material properties such as in particular its processing capability are not impaired in any way.

In an exemplary embodiment which has been found to be particularly suitable in practice, zirconium oxide is used as the contrast agent both for the spacer and for the liquid bone cement, and indeed with a weight-related proportion which is under 10% in each case (a problem free processing capability of the materials is hereby ensured), with the difference in concentration between the spacer and the liquid bone cement amounting to at least 3% by weight. The spacer and the liquid bone cement consist in this process of the same material which, in one embodiment, comprises PMMA, with the spacer containing approximately 2 to 5% by weight zirconium oxide and the liquid bone cement containing approximately 5 to 8% by weight zirconium oxide.

Provision is generally made in accordance with the invention for the spacer and the liquid bone cement to differ from one another with respect to their proportions, in particular related to weight or volume, or their concentrations of contrast agent.

It has been found that both a good contrast and a problem-free material processing can be achieved when the proportion or the concentration of contrast agent is lower in the spacer than in the liquid bone cement. The manufacturer of the spacer can thus also be carried out without problem by injection molding.

It is further proposed, in particular for reasons of processing capability, that the proportion of contrast agent in the spacer and in the liquid bone cement in each case does not exceed a maximum value of approximately 10%.

It was generally found that, in accordance with a further embodiment of the invention, a sufficiently good contrast is present when the difference between the two contrast agent proportions in the spacer and in the liquid bone cement amounts to at least approximately 3%, with this applying in particular on the use of zirconium oxide as the contrast agent, bone cement on a PMMA basis, weight-related proportions and an X-ray process.

Although not absolutely necessary, the spacer and the liquid bone cement can be provided with the same contrast agent.

Generally, any desired contrast agents can be used, with, for example, zirconium oxide (ZrO2) and/or barium sulfate (BaSO4).

Although generally any desired materials can be considered, the spacer and/or the liquid bone cement are, in one embodiment, made of a material comprising PMMA and in particular comprise a PMMA homopolymer, a PMMA copolymer or a mixture based on PMMA, e.g. PMMA/PS (polymethyl methacrylate/polystyrene).

The spacer and the liquid bone cement are, in one embodiment, produced from the same material.

Further embodiments of the invention are recited in the description and in the drawings.

Figure 2:
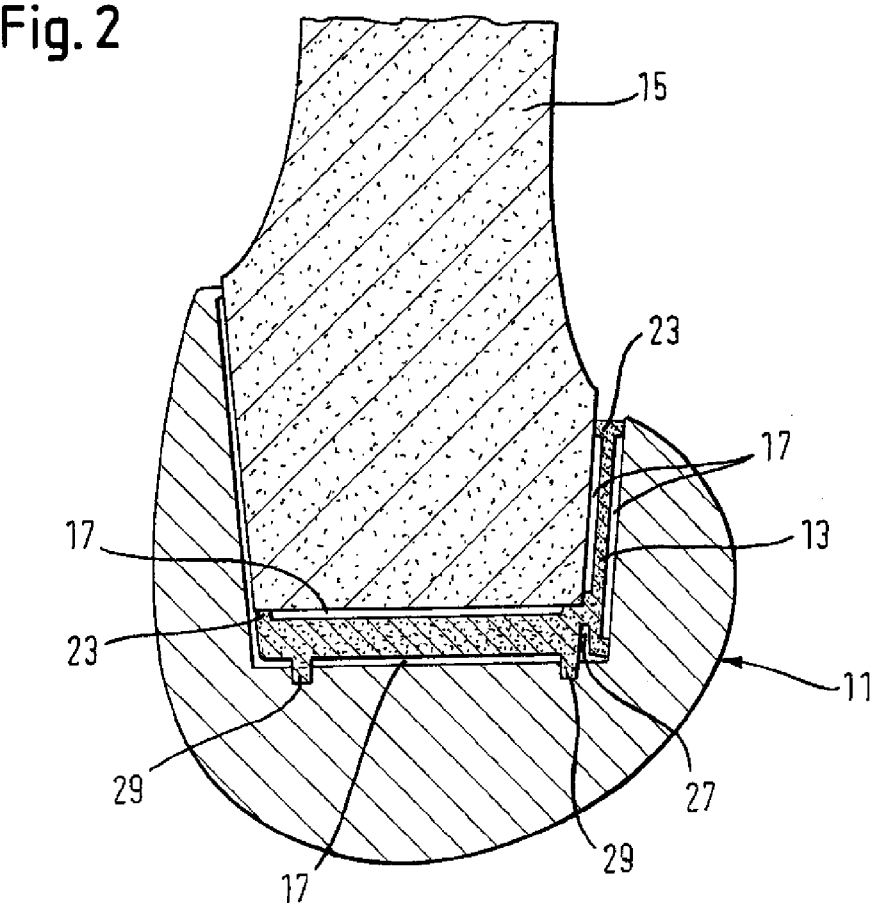
Figure 3:
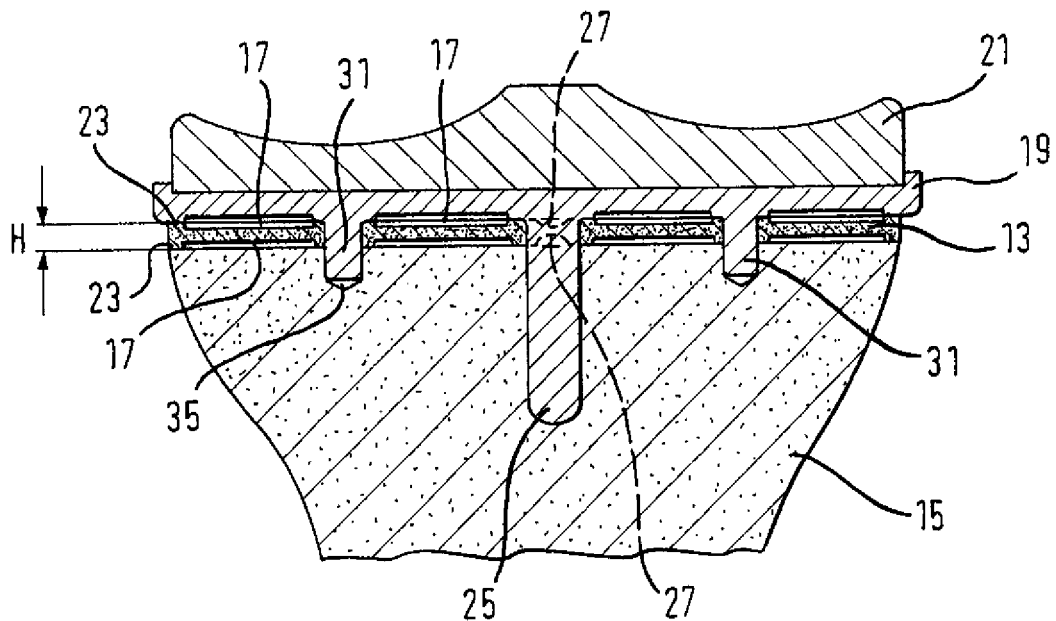

The invention will be described in the following by way of example with reference to the drawings. There are shown:

FIGS. 1 and 2 in each case an example for an application of the operation system in accordance with the operation, namely on the tibia (FIG. 1, sagittal section) and on the femur (FIG. 2, sagittal section);

FIG. 3 a frontal view of FIG. 1; and

Figure 4:
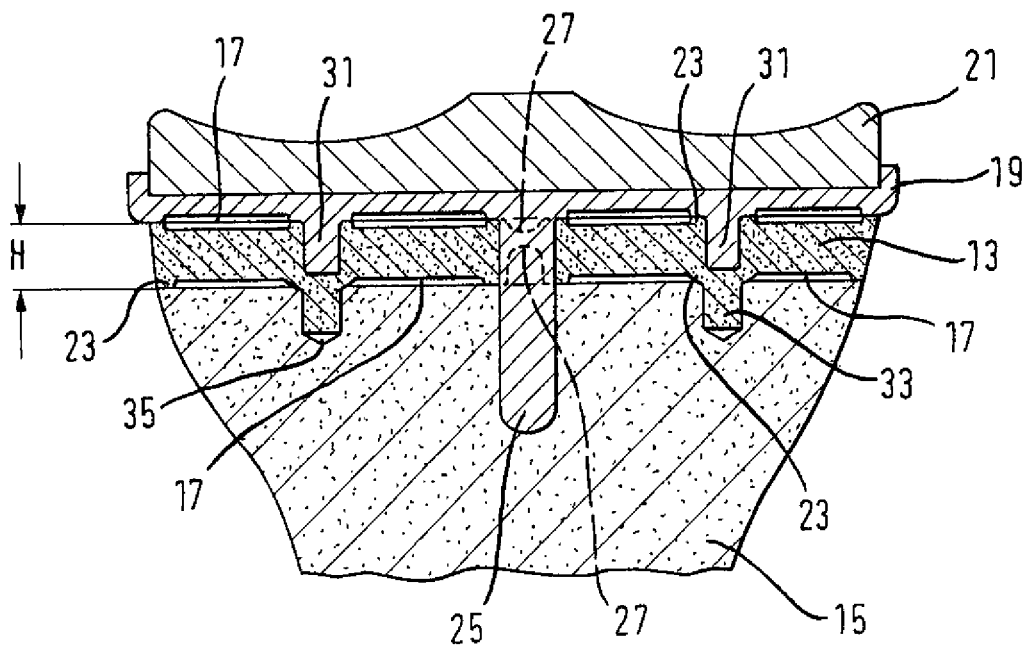

FIG. 4 a section analog to FIG. 3 with a thicker spacer.

FIG. 1 shows an exemplary operation system in accordance with the invention on a tibial bone 15. An implant 11 consisting of a support shell 21 and a tibial platform 19 provided with a stub 25 for anchoring in the bone 15 is a component of an artificial knee joint. A further component of this joint, namely a condylar prosthesis part at a femoral bone 15 cooperating with the support shell 21 is shown in FIG. 2 and likewise forms an implant 11 in the sense of the invention.

An areal distancing piece 13 also called a spacer in the following is arranged between the implants 11 and the bones 15 and serves for the position correction of the respective prosthesis part 11 at the bone 15 and has a specific height or thickness H for this purpose. A set of spacers 13 of different sizes and heights H is available to the surgeon. As FIG. 2 shows, the spacers 13 can also be made angled.

In one embodiment, the spacers 13 each consist of hardened bone cement on a PMMA base.

The spacers 13 are provided with one or more recesses at their upper sides and lower sides, whereby hollow spaces or intermediate spaces 17 are present between the spacer 13 and the bone 15 or between the spacer 13 and the prosthesis part 11. The hollows spaces or intermediate spaces 17 are fixed at the tibia (FIGS. 1, 3 and 4) by projections 23, e.g. in the form of a rib structure extending over the total respective surface. The projections 23 are each formed at the femur (FIG. 2) as a peripheral rib in the edge region, whereby in each case only a single hollow space or intermediate space 17 is present.

The angled spacer 13 in accordance with FIG. 2 is provided at one of its sides facing the implant 11 with centering pins 29 which cooperate with corresponding mounts in the prosthesis part 11 in order to provide a centering of the spacer 13 at the prosthesis part 11 in this manner.

The hollow spaces or intermediate spaces 17 serve for the reception of liquid bone cement with which the spacers 13 are fastened to the bone 15 and to the implant 11 in order hereby to firmly connect the implants 11 to the bone 15. Since the spacers 13 likewise consist of bone cement, a firm 30 homogeneous connection to the respective spacer 13 arises after the hardening of the liquid bone cement introduced into the spaces 17. The thickness of the cement layer is determined by the height h of the hollow spaces or intermediate spaces (FIG. 1).

To be able to distinguish the spacers 13 and the liquid cement respectively both from the surroundings and from one another for the monitoring of the operation in the X-ray, both the spacer 13 and the liquid cement are "dyed", i.e. provided with a contrast agent, in accordance with the invention, with the proportions of contrast agent in the spacer 13 and in the liquid cement, however, being selected to be different.

It can be recognized in FIG. 3 that, next to the central stub 25, centering spigots 31 project at both sides downwardly from the tibial platform 19 through cut-outs in the spacer 13 in order to align the spacer 13 to the platform 19, on the one hand, and to align the platform 19 and the spacer 13 overall to the bone 15 with respect to a rotation around the stub 25, on the other hand. Bores 35 are provided in the bone 15 for the centering spigots 31.

Furthermore, a sagittally extending break notch 27 is shown which has smaller dimensions than the cut-out for the stub 25 and which permits a halving intraoperatively so that also only half of the spacer 13 is centered by the stub 25 and the spigot 31. In this manner, with a resection incision stepped from lateral to medial, left hand and right hand spacer halves can be combined at a height H differing in accordance with the stepping, which reduces the number of the injection molds necessary for the manufacture. A different stepping can occur if really only defective bone tissue is taken into account in the resection.

To the left and to the right of the middle break notches 27 (FIG. 3), further break notches extending approximately parallel to the former can be provided so that the outer parts of the spacer can also be used as spacers in monocondylar applications.

A spacer 13 with a larger height H is shown in FIG. 4. The break notches 27 are made correspondingly deeper. In this process, the height H is so much larger than the projecting spigots 31 of the platform 19 that a spigot prolongation 33 is attached to the spacer 13 in the direction of the spigots 31, with bores 35 being provided in the bone 15 for the spigot prolongations 33.

In FIG. 2, a break notch 27 is likewise shown in the corner region of the angular spacer 13 which also permits the limbs of the angular spacers 13 to be used singly intraoperatively—in dependence on the bone cut.

The different possibilities in accordance with the invention to implement the principle in accordance with the invention specifically in practice were already discussed in the introductory part. The following embodiment has been found to be suitable in trials:

Spacer:
    Material: Bone cement on a PMMA base
    Contrast agent: 2-5 (e.g., 2) percent by weight zirconium oxide Liquid Bone Cement:
    Material: Like spacer
    Contrast agent: 5-8 (e.g., 7) percent by weight zirconium oxide

REFERENCE NUMERAL LIST 11 implant, prosthesis part
13 distance piece, spacer 15 bone
17 hollow space or intermediate space
19 tibial platform
21 support shell
23 projection
25 stub
27 break notch
29 centering pin
31 centering spigot
33 spigot prolongation
35 bore
H height of the spacer element
h height of the hollow space or intermediate space

The invention claimed is:

1. An implant system comprising:
a prosthetic implant;
a spacer sized for use with said prosthetic implant, said spacer including at least one outer surface formed from hardened bone cement, said spacer having a contrast agent incorporated therein at a first concentration chosen to achieve a first contrast; and
a curable fixative locatable between said spacer and said prosthetic implant to secure said spacer to said prosthetic implant, said curable fixative having a contrast agent incorporated therein at a second concentration chosen to achieve a second contrast, wherein said first concentration of the contrast agent in said spacer differs from said second concentration of the contrast agent in said curable fixative such that said first contrast differs from said second contrast to facilitate differentiating said spacer and said curable fixative from each other along said at least one outer surface of said spacer and to facilitate differentiating said spacer and said curable fixative from their surroundings.

2. The implant system of claim 1, wherein said spacer comprises a hardened bone cement and said curable fixative comprises a bone cement.

3. The implant system of claim 1, wherein said spacer and said curable fixative incorporate the same contrast agent.

4. The implant system of claim 1, wherein said first concentration of the contrast agent in said spacer is less than said second concentration of the contrast agent in said curable fixative.

5. The implant system of claim 1, wherein the contrast agent incorporated in said spacer and the contrast agent incorporated in said curable fixative are chosen to facilitate differentiation of said spacer from said curable fixative and their surroundings in an x-ray image of said spacer and said curable fixative.

6. The implant system of claim 1, wherein said first concentration of the contrast agent in said spacer and said second concentration of the contrast agent in said curable fixative is in each case limited to a maximum value of ten percent by weight.

7. The implant system of claim 1, wherein said first concentration of the contrast agent in said spacer is approximately 2 to 5 percent by weight and said second concentration of the contrast agent in said curable fixative is approximately 5 to 8 percent by weight.

8. The implant system of claim 1, wherein said first concentration of the contrast agent in said spacer is at least three percent by weight less than said second concentration of the contrast agent in said curable fixative.

9. The implant system of claim 1, wherein the contrast agent incorporated in said spacer and the contrast agent incorporated in said curable fixative are selected from the group consisting of zirconium oxide and barium sulfate.

10. The implant system of claim 1, wherein one of said spacer and said curable fixative include a polymer selected from the group consisting of polymethyl methacrylate, a polymethyl methacrylate homopolymer, a polymethyl methacrylate copolymer, or a mixture including polymethyl methacrylate.

11. The implant system of claim 1, wherein said spacer further includes a break notch, whereby said break notch permits reduction of the size of said spacer intraoperatively.

12. The implant system of claim 1, wherein said prosthetic implant is a femoral implant, wherein said spacer is adapted and configured to space said prosthetic implant from a femur.

13. The implant system of claim 1, wherein said prosthetic implant is a tibial implant, wherein said spacer is adapted and configured to space said prosthetic implant from a tibia.

14. The implant system of claim 1, wherein said curable fixative directly contacts said spacer and said prosthetic implant.

15. The implant system of claim 1, wherein said curable fixative directly contacts opposing first and second sides of said spacer.

16. An implant system comprising:
a prosthetic implant;
a spacer including at least one outer surface formed from hardened bone cement including a contrast agent at a first concentration chosen to achieve a first contrast; and
a curable bone cement including a contrast agent at a second concentration chosen to achieve a second contrast, wherein said first concentration of the contrast agent in said spacer differs from said second concentration of the contrast agent in said curable bone cement such that said first contrast differs from said second contrast to facilitate differentiating said spacer and said curable bone cement from each other along said at least one outer surface of said spacer and to facilitate differentiating said spacer and said curable bone cement from their surroundings, said curable bone cement locatable between said spacer and said prosthetic implant to secure said spacer to said prosthetic implant.

17. The implant system of claim 16, wherein said spacer and said curable bone cement incorporate the same contrast agent.

18. The implant system of claim 16, wherein said first concentration of the contrast agent in said spacer is less than said second concentration of the contrast agent in said curable bone cement.

19. The implant system of claim 16, wherein the contrast agent included in said spacer and the contrast agent included in said curable bone cement are chosen to facilitate differentiation of said spacer from said curable bone cement and their surroundings in an x-ray image of said spacer and said curable bone cement.

20. The implant system of claim 16, wherein said first concentration of the contrast agent in said spacer and said second concentration of the contrast agent in said curable bone cement are limited to a maximum of ten percent by weight.

21. The implant system of claim 16, wherein said first concentration of the contrast agent in said spacer is at least three percent by weight less than said second concentration of the contrast agent in said curable bone cement.

22. The implant system of claim 16, wherein the contrast agent included in said spacer and the contrast agent included in said curable bone cement are selected from the group consisting of zirconium oxide and barium sulfate.

23. The implant system of claim 16, wherein one of said spacer and said curable bone cement include a polymer selected from the group consisting of polymethyl methacrylate, a polymethyl methacrylate homopolymer, a polymethyl methacrylate copolymer, or a mixture including polymethyl methacrylate.

24. The implant system of claim 16, wherein said spacer further includes a break notch, whereby said break notch permits reduction of the size of said spacer intraoperatively.

* * * * *